United States Patent
Nicholson et al.

(10) Patent No.: US 8,095,387 B2
(45) Date of Patent: *Jan. 10, 2012

(54) METHOD OF PROVIDING ENHANCED HEALTH CARE AND PRESCRIPTION INFORMATION VIA CUSTOMIZED PRESCRIPTION MANAGER AND PORTABLE MEDICAL/PRESCRIPTION STATEMENTS

(75) Inventors: Christopher J. Nicholson, La Grange, KY (US); Jeanette R. Thomson, Louisville, KY (US); Darin A. Conn, Louisville, KY (US); Howard P. Shoaf, Louisville, KY (US); Michael T. Antonetti, Bellevue, WA (US)

(73) Assignee: Humana Inc., Louisville, KY (US)

( * ) Notice: Subject to any disclaimer, the term of this patent is extended or adjusted under 35 U.S.C. 154(b) by 815 days.

This patent is subject to a terminal disclaimer.

(21) Appl. No.: 11/642,237

(22) Filed: Dec. 20, 2006

(65) Prior Publication Data

US 2007/0192142 A1  Aug. 16, 2007

Related U.S. Application Data

(60) Provisional application No. 60/752,621, filed on Dec. 20, 2005.

(51) Int. Cl.
*G06Q 10/00* (2012.01)
*G06Q 50/00* (2012.01)
*A61B 5/00* (2006.01)
*G06F 19/00* (2011.01)

(52) U.S. Cl. .................................. 705/3; 705/2

(58) Field of Classification Search .................. 705/2, 3
See application file for complete search history.

(56) References Cited

U.S. PATENT DOCUMENTS

| | | | | |
|---|---|---|---|---|
| 4,991,877 A | * | 2/1991 | Lieberman | 283/36 |
| 7,444,291 B1 | * | 10/2008 | Prasad et al. | 705/2 |
| 2005/0033609 A1 | * | 2/2005 | Yang | 705/2 |
| 2005/0060199 A1 | * | 3/2005 | Siegel | 705/2 |
| 2006/0004612 A1 | * | 1/2006 | Chewning et al. | 705/4 |
| 2006/0212345 A1 | * | 9/2006 | Soza et al. | 705/14 |

OTHER PUBLICATIONS

NDC codes (A white paper giving a general overview and possible solutions associated with NDC's replacing HCPCS drug codes for institutional and professional billing. (May 3, 2001).*

* cited by examiner

*Primary Examiner* — Gerald J. O'Connor
*Assistant Examiner* — Neha Patel
(74) *Attorney, Agent, or Firm* — James C. Eaves, Jr.; Brian W. Chellgren; Greenebaum Doll & McDonald PLLC

(57) ABSTRACT

The present invention relates to a method of providing enhanced health care and medical prescription information via customized prescription manager and portable medical/prescription statements. The prescription manager and portable medical/prescription statements may cover periods of time and can be provided by mail or electronically, and can be provided routinely or at the request of the individual. The prescription manager and portable medical/prescription statements contain medication (i.e., prescription) history and other pertinent health care information. The portable medical/prescription statement is a prescription manager pocket insert which can be carried to a doctor's appointment, trip to the pharmacy, or simply to have readily available in the event of a medical emergency.

12 Claims, 6 Drawing Sheets

FIGURE 2A

Your Rx Manager ─ 10

HUMANA
Guidance when you need it most

March 31, 2005 to March 31, 2006 ─1      ─2      Jane Sample

Your Rx Manager is provided as a courtesy to help you manage taking and refilling your medications, and to communicate with your doctor or pharmacist about the medications you are taking. You may want to have this with you on your next visit with your doctor or pharmacy.

| YOUR REGULAR PRESCRIPTIONS ─3 |
|---|

Furosemide *(commonly used for: Heart)*

Strength: 40 mg        Quantity: 30 tablets        Pharmacy: Rite Aid
Category: Generic      Days supply: 30             Doctor: James Dean

| Refill dates | | | | | | | | | | | *Please fill in your next refill date* |
|---|---|---|---|---|---|---|---|---|---|---|---|
| Apr '05 | May '05 | Jun '05 | Jul '05 | Aug '05 | Sep '05 | Oct '05 | Nov '05 | Dec '05 | Jan '06 | Feb '06 | Mar '06 |
|  |  |  |  |  |  |  |  |  | 17th | 15th | 16th |

| *Your notes (include instructions, interactions and side effects):* |
|---|
|  |
|  |
|  |

Lipitor *(commonly used for: Cholesterol)*

Strength: 10 mg             Quantity: 15 tablets        Pharmacy: Brooks Pharmacy
Category: Preferred brand   Days supply: 30             Doctor: James Dean

| Refill dates | | | | | | | | | | | *Please fill in your next refill date* |
|---|---|---|---|---|---|---|---|---|---|---|---|
| Apr '05 | May '05 | Jun '05 | Jul '05 | Aug '05 | Sep '05 | Oct '05 | Nov '05 | Dec '05 | Jan '06 | Feb '06 | Mar '06 |
|  |  |  |  |  |  |  |  |  | 14th | 12th | 14th |

| *Your notes (include instructions, interactions and side effects):* | ⓘ Formulary change: |
|---|---|
|  | On July 1, 2006 your cost will increase. Lovastatin is available for a lower cost with your plan. |

Protonix *(commonly used for: Stomach)*

Strength: 40 mg                Quantity: 90 tablets        Pharmacy: Albertsons
Category: Non-preferred brand  Days supply: 90             Doctor: Donna Fields

| Refill dates | | | | | | | | | | | *Please fill in your next refill date* |
|---|---|---|---|---|---|---|---|---|---|---|---|
| Apr '05 | May '05 | Jun '05 | Jul '05 | Aug '05 | Sep '05 | Oct '05 | Nov '05 | Dec '05 | Jan '06 | Feb '06 | Mar '06 |
|  |  |  |  |  | 10th |  |  | 4th |  |  | 5th |

| *Your notes (include instructions, interactions and side effects):* | $ Lower cost alternatives: |
|---|---|
|  | - Omeprazole (generic) |
|  | - Zantac |

FIGURE 2B

Your Rx Manager             HUMANA

OTHER OCCASIONAL PRESCRIPTIONS — 4

Amoxicillin *(commonly used for: Antibiotics)*

Strength: 500 mg    Category: Generic    Date filled: Jan 23 '06
Quantity: 4 capsules    Pharmacy: Brooks Pharmacy
Days supply: 1    Doctor: Donna Fields

Dexamethasone *(commonly used for: Steroids)*

Strength: 4 mg    Category: Generic    Date filled: Mar 2 '06
Quantity: 39 tablets    Pharmacy: Brooks Pharmacy
Days supply: 12    Doctor: Donna Fields

Oxycodone w/Acetaminophen *(commonly used for: Pain management)*

Strength: 5-325 mg    Category: Generic    Date filled: Mar 28 '06
Quantity: 120 tablets    Pharmacy: CVS
Days supply: 15    Doctor: Donna Fields

ADDITIONAL MEDICATIONS & NOTES — 5

Please use this space to write your own notes.

Other medications you take

| Over-the-counter drugs | Medication samples | Vitamins and supplements |
|---|---|---|
|  |  |  |
|  |  |  |
|  |  |  |
|  |  |  |
|  |  |  |

Reactions and allergies

| Food | Medications | Other substances (latex etc.) |
|---|---|---|
|  |  |  |
|  |  |  |
|  |  |  |
|  |  |  |
|  |  |  |

Visits with your doctor

| Questions for your doctor | Instructions from your doctor |
|---|---|
|  |  |
|  |  |
|  |  |
|  |  |
|  |  |

FIGURE 3

Front of Card 1 6
✂ CUT CARDS ALONG DOTTED LINES AND FOLD ON AS INDICATED

Emergency contact
Name: _____
Phone: _____

My pharmacy and doctor
Name: _____
Phone: _____
Name: _____
Phone: _____

FOLD

Your Rx Record On-the-Go is provided as a courtesy to help you manage your medications, and to communicate with your doctor or pharmacist. Humana makes this information available for the sole purpose of providing educational information on health-related issues. It is not intended to be a substitute for professional medical advice. This card does not imply evidence of coverage with Humana.

FOLD

Humana Rx Pocket Pal

Name
Jane A. Sample

Member ID
99999999

HUMANA.    For
Oct 1 '04 to Oct 31 '05

---

Back of Card 2 7

8 — Regular prescriptions   Qty   Dosage
Furosemide   30   40 mg
Lipitor   15   10 mg
Protonix   90   40 mg
Drug name...   ...   ...

FOLD

Other drugs I take
_____
_____
_____

Reactions or allergies
_____
_____
_____

FOLD

- Over-the-counter medicines, and even some foods, can interact with your medications. Talk to your pharmacist if you have questions or concerns.

- You may save time and money by having prescriptions delivered to your home. Call [1-866-255-7451 between 8 a.m. – 8:30 p.m. EST, Mon-Fri (TDD 1-800-833-3301)] for mail order details.

45, 9, 46, 47

METHOD OF PROVIDING ENHANCED HEALTH CARE AND PRESCRIPTION INFORMATION VIA CUSTOMIZED PRESCRIPTION MANAGER AND PORTABLE MEDICAL/PRESCRIPTION STATEMENTS

This application claims the benefit of U.S. provisional patent applications Ser. No. 60/752,621, filed Dec. 20, 2005, titled Method of Providing Enhanced Healthcare Prescription Information via a Customized Prescription Manager and Portable Medical Record, the provisional application incorporated herein by reference.

BACKGROUND OF THE INVENTION

Field of the Invention

The present invention relates to a method of providing enhanced health care and prescription information via a customized prescription manager and portable medical/prescription statements. The prescription manager and medical/prescription statements can be appended to any personal health finance and benefits statement, provided with other documents, or provided as stand-alone documents. The personal health finance and benefits statement is provided to each member of the healthcare plan provider by the healthcare provider. The prescription manager contains prescription information and other pertinent healthcare information, and the portable medical/prescription record can be detached and brought along with the member to a doctor's visit, trip to the pharmacy, or to have readily available in the event of an emergency. The prescription manager and portable medical record may cover particular periods of time, may be provided by mail or electronically, and may be provided routinely or at the request of the individual.

SUMMARY OF THE INVENTION

The present invention relates to a method of providing enhanced health care and prescription information so that the consumers of health care can make more informed decisions related to their health. Individuals who use health care services are often covered by insurance plans, which may cover some medical and pharmacy expenses. These individuals often decide which doctor or medical facility they will visit for services. In consultation with their medical providers, they receive prescriptions for various drugs and then must select the pharmacy to use to fill these prescriptions.

It is the purpose of the present invention to provide the consumers of health care with reliable and accurate information about their prescription history and medical record, which can be easily carried with the consumer, particularly as a reference during doctor visits and trips to the pharmacy. This is accomplished by providing a paper or electronic customized prescription manager and portable medical record, which may be attached and distributed to consumers along with a personal health finance and benefit statement, provided by the healthcare plan provider (i.e., insurer) or even distributed to the consumer separately as a stand alone record. This prescription manager and portable medical record can be provided periodically, for example quarterly or monthly, by the health care insurer, along with the personal health finance and benefit statement. Alternatively, the prescription manager and portable medical record can be provided at the request of the consumer. The power of these tools is in their ability to clearly list the medications the member or consumer is currently taking. Having such a list of the medications is beneficial in case of an emergency, to discuss with the member's doctor and pharmacist, or to refill a prescription. The member can retrospectively review their past prescriptions in order to more effectively plan and prepare for future health care events and costs. The recipient has the option of detaching certain portions of the portable medical record (i.e., a prescription pocket insert), which may contain prescription information and/or other healthcare information, to carry with the member in a portable credit-card sized packet.

Even more specifically, the present invention is for a method of providing prescription information to a health care plan member, the method comprising the following steps: a. maintaining prescription claim data on at least one plan member; b. extracting from the prescription claim data maintained information needed to produce a personal prescription statement for at least one plan member; c. utilizing one of at least one statement templates to complete a personal prescription statement for each of the at least one plan member for which information was extracted: (1.) inserting the extracted information appropriately into the statement template to identify that at least one plan member and to reflect to that at least one plan member that member's regular prescription information; and, (2.) inserting into the statement template at least one marker with associated information related to the inserted extracted information to highlight that associated information to that at least one plan member; and d. providing that at least one plan member with their completed statement. The marker can include at least one of a savings alert marker, a health alerts marker, a plan alert marker, a personalization marker, an online resources marker, and a phone resources marker.

For regular prescriptions and/or occasional prescriptions, any of quantity, dosage information drug category, days supply, pharmacy, doctor information, or refill date(s) can be provided. Also, a pictorial representation of each prescription drug listed can be provided to assist that member in drug identification.

The personal prescription statement can include a location for that member to annotate other drugs that member takes and to annotate drug reactions and allergies. The personal prescription statement can have indicia identifying where the statement can be folded to form a credit card size statement. The personal prescription statement can include prescription information for a previous period of time, for example, for twelve months. The statement can also include disclaimer information.

There are many possible delivery methods for the personal prescription statement. For example, the step of providing the completed statement can be accomplished electronically. The at least one plan member can view their completed statement via a member portal on the Internet. The at least one plan member can be notified by electronic mail that their completed statement is available for viewing at the member portal. Also, the step of providing the at least one plan member with their completed statement can be accomplished by printing the statement and mailing it to that at least one plan member.

BRIEF DESCRIPTION OF THE DRAWINGS

A better understanding of the present invention will be had upon reference to the following description in conjunction with the accompanying drawings, wherein:

FIGS. 2A-2B show a sample of a prescription manager statement which may be attached with a personal health finance and benefit statement; and, FIG. 3 shows a sample of the front side of a first and the back side of a second portable medical/prescription statement, the first and second statements being two copies of the same statement, the back side of the first statement being identical to the back side of the second statement shown but printed on the reverse side of the first statement front side, and the front side of the second statement being identical to the front side of the first statement shown but printed on the reverse side of the second statement back side.

DETAILED DESCRIPTION OF THE PREFERRED EMBODIMENT

With reference to FIGS. 1A-1C, 2A-2B and 3, the method of providing enhanced health care information through the collection and processing of prescription data to produce the customized prescription manager and portable medical/prescription statements (i.e., prescription pocket insert) is shown and described. The prescription manager and portable medical/prescription use information available to Humana Inc. (hereinafter Humana) from member data, processed medical and pharmacy claims, from spending accounts managed by Humana, third party providers, commercial groups and from other available information. The present invention relates to a method of providing enhanced health care and prescription information so that the consumers of health care can make more informed decisions related to their health.

Figure 1A:
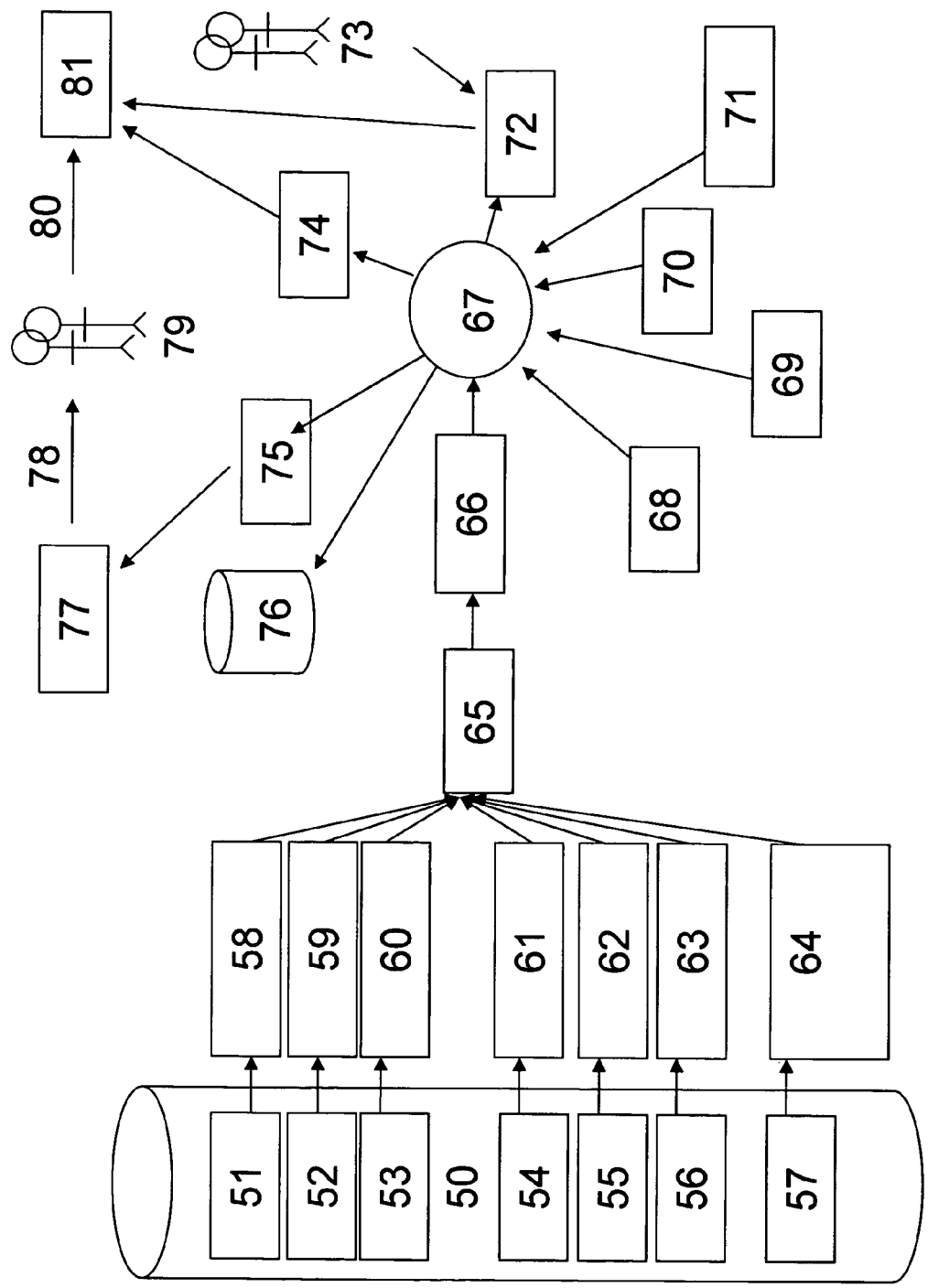
FIGS. 1A-1C demonstrates the architecture involved in obtaining information used and in producing the prescription manager and portable medical/prescription statement.
Figure 1B:
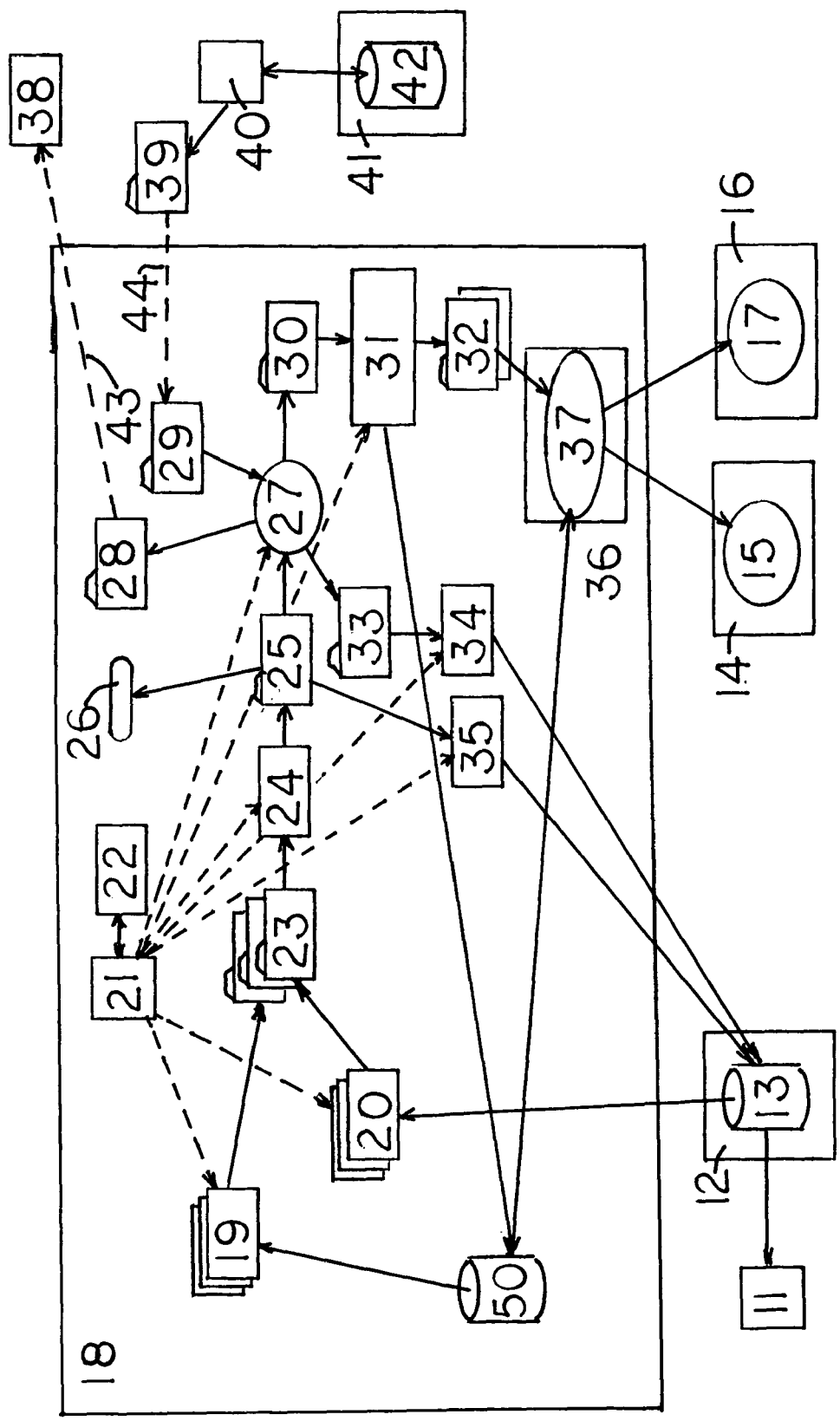
Figure 1C:
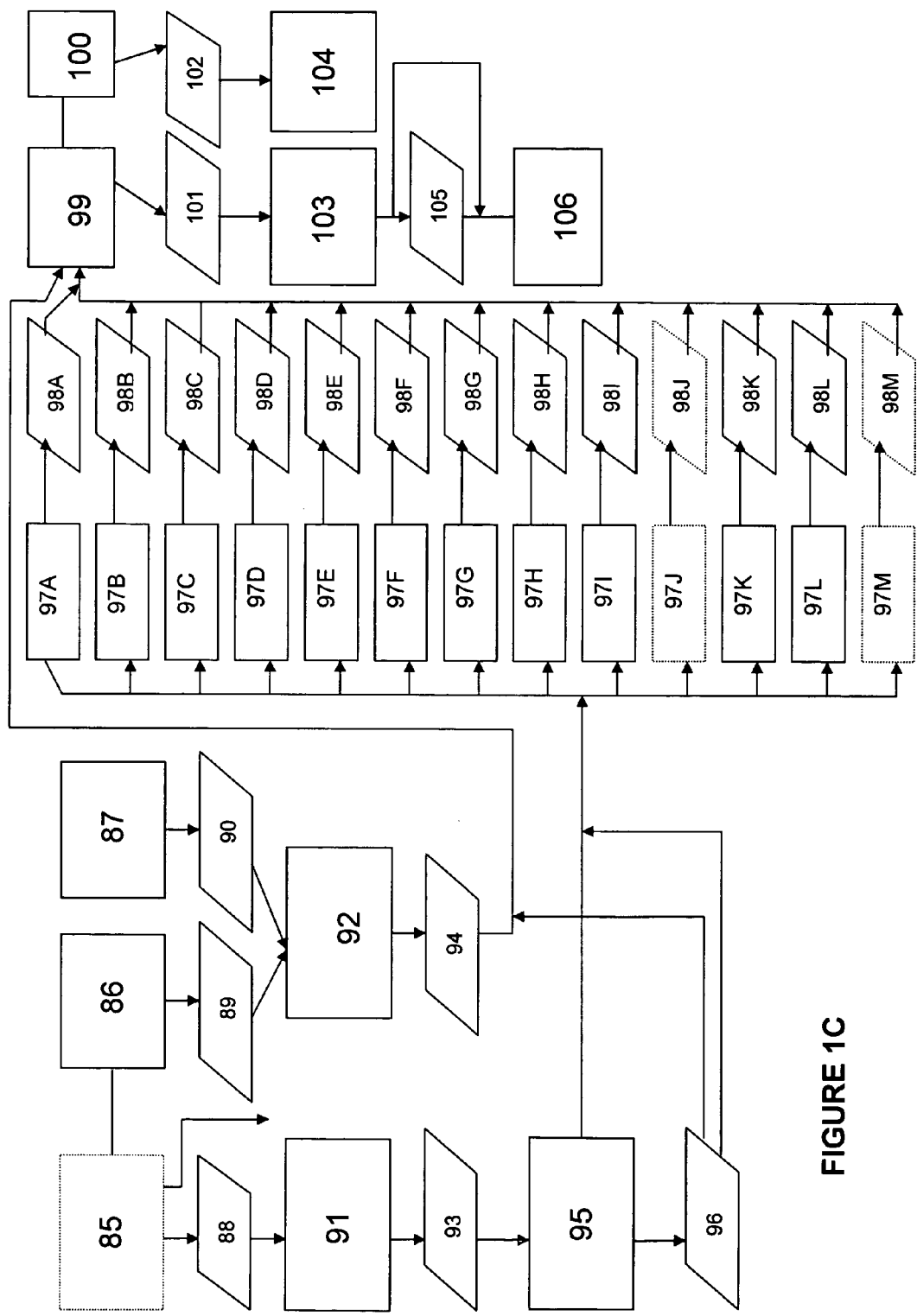

The architecture shown in FIGS. 1A-1C shows the data available in the Humana operational data store (ODS), a mineable data asset. The diagram displays data at a high level and may not represent all possible data that may be used to produce the statement. FIG. 1A shows Humana's Integrated Customer Experience (ICE) Summary Statement Architecture; FIG. 1B shows Humana's ICE Statement Logical Deployment/Execution Architecture; and FIG. 1C shows the Summary Statement Extract Flow Diagram. The following legend is used in FIGS. 1A-1C: 11—Discoverer; 12—Computer Server; 13—Electronic Data Warehouse (EDW); 14—Web Server; 15; Customer Service Representative (CSR) Portal; 16—Web Server; 17—Member Portal; 18—Mainframe; 19—ODS Extracts; 20—EDW Extracts; 21—Process Verification; 22—Process Control; 23—Intermediate Files; 24—Flat File Creation Process; 25—Flat File; 26—Tape Archive; 27—Dialogue; 28—Advanced Function Printing (AFP); 29—Template; 30—Portable Document Format(PDF); 31—PDF Post Process; 32—PDF; 33—Messages Sent; 34—Message Tracking Process; 35—Key and Calculation Logging Process; 36—WebSphere Application Server; 37—Web Service; 38—Print Facility; 39—Template; 40—Exstream Designer; 41—Windows 2000 Server; 42—Structured Query Language(SQL) Server; 43—Secure FTP; 44—FTP; 50—Operational Data Storage (ODS); 51—Customers; 52—Members; 53—Benefits; 54—Medical Claims; 55—Rx Claims; 56—Flexible Spending Accounts (FSA) / Personal Care Accounts (PCA) / Health Savings Accounts (HSA) / Limited Access Accounts (LAA); 57—Disease Management Programs; 58—Customer Extract; 59—Member Extract; 60—Benefits Extract; 61—Medical Claims Extract; 62—Rx Claims Extract; 63—Reimbursement Accounts Extract; 64—Disease Management Extract; 65—Composition Engine Input Assembly Process; 66—Composition Engine Input; 67—Composition Engine; 68—Statement Template; 69—Customer Supplied Content; 70—Images; 71—Personalized Content (Humana and/or 3rd Party); 72—Statement PDF; 73—Customer Service Representatives; 74—Statement Hyper Text Markup Language (HTML); 75—Printer; 76—Message Tracking; 77—Printed Personalized Statement; 78—Mailed to 79—Humana Members; 80—Views statement; 81—Member Portal on Internet; 85—Group Inclusion Process; 86—Group Level Data Extract Process (account info); 87—Group Level Data Extract Process (clinical program info); 88—Inclusion File; 89—Group Level Data File 1; 90—Group Level Data File 2; 91—Member Eligibility and Benefits (E&B) Process (includes medical & Rx Benefits); 92—Combine Group Level Data files; 93—Member Eligibility (ME) E&B Standard File; 94—Combined Group Level Data File; 95—Transform ME info to Integrated Consumer Experience Team(ICE) format; 96—ICE format of ME data; 97A—Med Claim Extract; 97B—Accumulations Extract; 97C—Medical Portable Health Record (PHR) Extract; 97D—Rx Claim Extract; 97E—Rx PHR Extract; 97F—Account Balance Data Extract; 97G—Account Transaction Data Extract; 97H—Member Preferences Extract; 97I—Customer Service Call Data Extract; 97J—Premium Data Extract; 97K—Clinical Condition Extract; 97L—Clinical Program Participation Extract; 97M—Previous Message Extract (possible future need); 98A—Medical Claim Data; 98B—Accumulations Data; 98C—Medical PHR Data; 98D—Rx Claim Data; 98E—Rx PHR Data; 98F—Account Balance Data; 98G—Account Transaction Data; 98H—Member Preferences Data; 98I—CSR Data; 98J—Premium Data; 98K—Clinical Medical Condition Code (MCC) Data; 98L—Clinical Program Data; 98M—Message Data; 99—Merge & Sort Process; 100—Extract Data for Data Mining; 101—Dialogue Input File; 102—Key & Calculation Data File; 103—Dialogue Process; 104—Update EDW with Key Information; 105—Message Data; and 106—Update EDW with Message Data.

The data can be obtained or extracted from the ODS 50 on a periodic basis or on demand. Examples of data extracted from the ODS or obtained from other sources are: identification of the member's insurance group; member identification information, including member identification number, member name and address information; information about the medical and pharmacy benefits to which the member is entitled; information about filed medical and pharmacy claims; information about the member's health account, including contributions and expenditures; information about any programs in which the member is enrolled; information about any medical category in which the member has expressed interest; information about any premiums received from the member's employer, and articles or content sourced from an internal or external content provider.

Specific data extracts will run to pull the data necessary for generation of personal health finance and benefit statements, customized prescription managers and portable medical/prescription statements. The output of the data extracts will be assembled into a flat file by an assembly process. The flat file will be used by a composition engine to create the statement, prescription manager statement, and portable medical/prescription statement. The data extracts and assembly process will apply business rules and calculations to create additional data elements to drive personalization. For example, personal demographics may be compared against claims history to identify whether or not an age-, sex- or condition-based message should appear on the statement and prescription manager. This particular message may direct the member toward a specific procedure or behavior change. This kind of comparison may also determine the type of article or guidance-based content that appears on the statement.

Additionally, current results may be compared to or displayed alongside the results of prior period results. For example, for account-based information, current health account balances may be compared to past account balances to demonstrate level of usage, remaining balances, etc. Once the resulting data is directed to the composition engine, additional rules, similar to the ones previously described, may be applied. The composition engine will consolidate the data with the statement template to produce the periodic statement, prescription manager and medical record. Because data will vary from member to member, the results will be unique for each member. The resulting statement, prescription manager statement, and portable medical/prescription statement will be available for print distribution or for display in an electronic environment as a PDF file or other file type. The resulting member data may also be available to present in an HTML format on a website or other electronic delivery vehicle. The statements, prescription manager statements and portable medical/prescription statements can be produced periodically as a batch process—for example, monthly, quarterly—or by plan year, or dynamically and upon request. The architecture of FIGS. 1A-1C shows further how Humana designs the layout and produces the statement, prescription manager statement, and portable medical/prescription statement.

This member's prescription manager 10 shown in FIGS. 2A and 2B is preferably extracted from both the member medical and pharmacy claim information pertaining to medical prescriptions. The prescription manager identifies prescribed medications from the pharmacy claim database. The prescription manager can optionally be added to any of the health care finance and benefits statements produced by Humana. Together they provide a personal health care record and a prescription record for this member for a period of time to assist members in tracking and managing their prescriptions.

As shown in FIG. 2A at 1, for this member, the records are provided for a year period: Mar. 31, 2005, to Mar. 31, 2006. This prescription manager statement, which assists the member in managing interactions with healthcare providers such as physicians and hospitals, compiles twelve months of health care services, integrating medical and pharmacy in one linear chronological view.

The prescription manager statement is driven from the claims detail outlined from different health plans provided by Humana. The purpose is to provide a rolling history of prescriptions for members. The information will vary based on utilization.

At the top of FIG. 2A is a messaging zone 2 that will be used for general health guidance or section explanation. For example, for a first time recipient, the messaging zone 2 could state "Your Rx Manager is provided as a courtesy to help you manage taking and refilling your medications, and to communicate with your doctor or pharmacist about the medications you are taking. You may want to have this with you on your next visit with your doctor or pharmacy."

Further, FIG. 2A shows managed medications 3, including the condition the member has (e.g., heart, stomach, high blood pressure and cholesterol), the medication the member takes, quantity, dosage, days supply, number of times the prescription has been filled, the last date the prescription has been filled, the next prescription refill date, the doctor that prescribed the medication, and the pharmacy where the prescription was filled, all in an easy-to-read format. A picture of the medication may also be included for ease of reference, if possible, as well as a "notes" section for jotting down instructions, interactions, side effects, and other drugs taken, for example. There may be an optional "refill dates" section in which the member can fill in the date of his next refill each month. There will also optionally be a messaging zone that will be used for general health guidance or section explanation near the bottom of the page.

As shown in FIG. 2A, this plan member has three regular prescriptions. The first drug, furosemide is commonly used for the heart. The 40 mg strength, generic category, 30 tablet quantity, 30 day supply, filling pharmacy Rite Aid, and prescribing Doctor James Dean are listed along with a picture of the drug. Also, the dates the prescription has been filled are listed along with a place for the plan member to note when the next refill should occur. There is also a location for the plan member to make notes, which the member may want to share with their doctor or pharmacist. In this notes section, notes about the drug could be provided, although there are none for this furosemide. The second drug, lipitor is commonly used for cholesterol. The 10 mg strength, preferred brand category, 15 tablet quantity, 30 day supply, filling pharmacy Brooks Pharmacy, and prescribing Doctor James Dean are listed along with a picture of the drug. Also, the dates the prescription has been filled are listed along with a place for the plan member to note when the next refill should occur. There is also a location for the plan member to make notes, which the member may want to share with their doctor or pharmacist. In this notes section, notes about the drug are provided. Here there is an attention marker, an exclamation mark or "!", provided to draw the member's attention to this notice of a formulary change. This marker and note tells the member that "On Jul. 1, 2006, your cost will increase. Lovastatin is available for a lower cost with your plan." The third drug, protonix is commonly used for the stomach. The 40 mg strength, non-preferred brand category, 90 tablet quantity, 90 day supply, filling pharmacy Albertsons, and prescribing Doctor Donna Fields are listed along with a picture of the drug. Also, the dates the prescription has been filled are listed along with a place for the plan member to note when the next refill should occur. There is also a location for the plan member to make notes, which the member may want to share with their doctor or pharmacist. In this notes section, notes about the drug are provided. Here there is an attention marker, a dollar sign or "$", provided to draw the member's attention to this notice of lower cost alternatives. This marker and note alerts the member that a generic drug omeprazole or zantac are lower cost alternatives to this protonix.

FIG. 2B shows non-managed medications, such as other occasional prescriptions 4 and additional medications 5, including information such as the medication the member takes, quantity, dosage, days supply, number of times the prescription has been filled, the next prescription refill date, the doctor that prescribed the medication, and the pharmacy where the prescription was filled, all in an easy to read format. A picture of the medication may also be included for ease of reference.

As seen in FIG. 2B, this plan participant has three occasional prescriptions, amoxicillin, an antibiotic; dexamethasone, a steroid; and oxycodone with acetaminophen, for pain management. For each, the strength, the quantity, the days supply, the category, the pharmacy filling, the doctor prescribing, and the last date filled, along with a picture of the drug are provided.

An "additional medications and notes" section 5 provides a space for the member to list other medications, including over-the-counter drugs, medication samples, and vitamins. Reactions and allergies to food, medications, and other substances can be noted in another section. A section may also be included to jot notes before, during and/or after doctor visits, including questions for the member's doctor and instructions from the doctor.

The list of medications presented in FIGS. 2A and 2B compiles all the prescription medications, managed and non-managed, a member has used in the past twelve months and lists them together, to provide a portable record members can take with them to their next physician appointment to give the physician a broader view of the member's healthcare interactions, instead of physically taking in all the medications to the physician appointment.

FIG. 3 show a sample of the front side of a first and the back side of a second portable medical/prescription statement, the first and second statements being two copies of the same statement, the back side of the first statement being identical to the back side of the second statement shown but printed on the reverse side of the first statement front side, and the front side of the second statement being identical to the front side of the first statement shown but printed on the reverse side of the second statement back side. This foldable or pocket/wallet statement can be printed front to back like this where two copies are provided. Also, the front and back shown in FIG. 3 could be moved together and printed one sided so that the member first folded the card down the middle and then at the three fold lines. The printing can be done on any desired paper thickness.

As stated, FIG. 3 shows the front of a first portable medical/prescription statement 6 and the back of a second portable medical/prescription statement 7. The statements are identical and, in this situation, the plan member, "Jane A. Sample", is being provided with two identical statements. These statements 6 and 7 are printed front and back so that what is shown for the back of the second card is printed on the reverse side of the front of the first card and what is shown for the front of the first card is printed on the reverse side of the back of the second card. In this format, these two identical statements can optionally be added to any of the health care finance and benefit statements, or with other materials, or provided as a stand-alone document. The statement cards 6 and 7 of FIG. 3 can be removed from the page and folded into a pair of credit-card sized pocket inserts, which the member can carry with him to doctor appointments or pharmacies, or to have as a quick reference in case of a medical emergency. Such a credit card sized pocket insert is not as cumbersome to carry around as traditional medical records. As shown on the back of the second card 7, a list of the medications 8 the member has been prescribed and the quantity and dosage of each is provided. Here, this member is shown having regular prescriptions for furosemide, lipitor, and protonix in the quantities and dosages listed. Below this list of prescribed drugs, there is a place for the member to list other drugs the member takes. For example, the member could list over the counter meds here. There is also a place for the member to list drug reactions or allergies. As with the Rx Manager 10, this pocket statement employees markers 47 to highlight information for the member. As seen at the bottom of the back of the second card, two markers are utilized. A "stethoscope" marker notes that "over-the counter medicines, and even some foods, can interact with your medications. Talk to your pharmacist if you have questions or concerns." A "$" of dollar sign savings alert marker states that "you may save time and money by having prescriptions delivered to your home" and provides contact information for further details.

Before discussing the front of the first card 6, more information is provided on the possible markers that can be used with either of the statements of this invention. The "$" marker, already discussed, represents savings alerts or opportunities for you to save money next time. The "stethoscope" marker, already discussed, represents health alerts and provides tips for maintaining or improving your health in the future. The "meshing gears" marker represents how the member's plan works and provides information about how the member's plan applies to their specific services. The "!" marker, already discussed, includes prescription coverage changes, such as notice of upcoming changes to copays or coverage for medications you take. It can also include plan deadlines or reminders of dates to submit information or take action. A "checklist" marker represents personalization or opportunities for the member to set preferences for his statement and other communications and services. A "computer mouse" marker represents online resources or Web tools to help the member get what he needs when he needs it. A "telephone handset" marker represents phone resources or phone tools to help the member get what he needs when he needs it. Any other desired markers can be used, as these symbols are examples only. Any symbol can be used for these defined markers and additional markers can be included for highlighting other areas for the member. For example, a "lock" marker can be used to identify information related to privacy of information.

Now turning back to the information on the front of the first card 6. Key medical contact information 9 can be recorded on the page, such as emergency contact name and phone and pharmacy and doctor name and phone. The page further includes product disclaimer text 45, and information 46 related to the health insurance plan, including the member's name, the member's ID, and the relevant time period. This page can be perforated so that the member can detach cards 6 and 7, and fold "marks" prompt the member to fold the detached cards 6 and 7 in particular areas so that they can be formed into the portable credit-card-sized pocket inserts. As shown, multiple copies may be provided for the member's convenience. Alternatively, a single front to back copy can be provided or a side to side copy can be provided where the front and back of the card are only printed on one side of a page.

The member prescription manager and medical/prescription statements shown in FIGS. 2A-2B and 3 provide extensive information on a member's health care experiences and information which is tailored to that member's prescription history, and the health care consumer will be a better educated consumer of health services and be able to make more informed decisions. The prescription manager and the portable medical/prescription statements can be mailed to each member for months in which prescription drug benefits are provided or when a formulary change notice is required. Alternatively, these statements can be provided electronically.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method of providing prescription information to a health care plan member, the method comprising the following steps:
   a) providing an operational data storage maintaining prescription claim data on at least one plan member;
   b) extracting from said prescription claim data maintained information needed to produce a personal prescription statement for at least one plan member;
   c) creating additional data elements relevant to said at least one plan member by applying business rules and calculations to said extracted information, wherein the step of creating said additional data elements comprises comparing personal demographics of said at least one plan member against claims history of said at least one plan member to identify, based on at least one of said at least one plan member's age, sex, or condition, a message to include in a personal prescription statement;

d) providing at least one prescription statement template for producing a personal prescription statement readable by said at least one plan member;

e) receiving said extracted information, said additional data elements, and one of at least one prescription statement template as inputs into a composition engine, said composition engine creating said personal prescription statement for each of said at least one plan member for which information was extracted:

(1) inserting said extracted information appropriately into said prescription statement template to identify that said at least one plan member and to reflect to that said at least one plan member that member's regular prescription information and occasional prescription information;

(a) where said personal prescription statement includes prescription information for a previous period of time;

(b) where said extracted information relevant to that said at least one plan member inserted into said prescription statement template also reflects for said regular prescriptions refill dates during said previous period of time;

(c) where said prescription statement template also reflects for said regular prescriptions quantity, dosage, drug category, days supply, pharmacy, and doctor information and where a visual representation of each prescription drug listed is provided to assist that member in drug identification;

(d) where said prescription statement template also reflects for said occasional prescriptions quantity, dosage, days supply, drug category, pharmacy, doctor, and date prescription filled information and where a visual representation of each prescription drug listed is provided to assist that member in drug identification; and, (e) where said prescription statement template includes a location for that member to annotate other drugs that member takes and to annotate drug reactions and allergies; and, (2) inserting into said prescription statement template at least one pictorial marker with associated information related to said inserted extracted information to highlight that associated information to that said at least one plan member, where said at least one pictorial marker includes at least one of a savings alert marker, a health alerts marker, a plan alert marker, a personalization marker, an online resources marker, and a phone resources marker;

(3) inserting one of general health guidance information and section explanation information into a messaging zone in said personal prescription statement;

(4) inserting said message of step c) into said personal prescription statement; and, f) providing that said at least one plan member with their completed statement;

said personal prescription statement being a document comprising:

said messaging zone including one of general health guidance information and section explanation information;

a regular prescription section including quantity, dosage, drug category, days supply, pharmacy, and doctor information for that said at least one plan member's regular prescriptions, and a representation of each listed prescription drug to assist that member in drug identification;

an occasional prescription section including quantity, dosage, drug category, days supply, pharmacy, and doctor information for that said at least one plan member's occasional prescriptions, and a representation of each listed prescription drug to assist that member in drug identification;

an additional medication section including information regarding medications not included in said regular prescription section and said occasional prescription section; and at least one notes section for at least one of said at least one plan member and provider of said personal prescription statement to include additional information.

2. The method of claim 1, where said at least one pictorial marker includes at least one of a savings alert marker, an online resources marker, and a phone resources marker.

3. The method of claim 1, where said personal prescription statement includes a location for that member to annotate other drugs that member takes and to annotate drug reactions and allergies.

4. The method of claim 1, where said personal prescription statement has indicia indication where the statement can be folded to form a credit card size statement.

5. The method of claim 1, where said personal prescription statement includes prescription information for a previous period of time.

6. The method of claim 5, where said previous period of time is twelve months.

7. The method of claim 5, where said extracted information relevant to that said at least one plan member inserted into said prescription statement template also reflects for said regular prescriptions refill dates during said previous period of time.

8. The method of claim 1, where the personal prescription statement includes disclaimer information.

9. The method of claim 1, where the step of providing that said at least one plan member with their completed statement is accomplished electronically.

10. The method of claim 9, where that said at least one plan member views their completed statement via a member portal on the Internet.

11. The method of claim 10, where that said at least one plan member is notified by electronic mail that their completed statement is available for viewing at said member portal.

12. The method of claim 1, where the step of providing that said at least one plan member with their completed statement is accomplished by printing the statement and mailing it to that said at least one plan member.

* * * * *